United States Patent [19]

Wagner

[11] 4,239,972
[45] Dec. 16, 1980

[54] DEVICE FOR COMPUTED TOMOGRAPHY

[75] Inventor: Wolfgang Wagner, Hamburg, Fed. Rep. of Germany

[73] Assignee: U.S. Philips Corporation, New York, N.Y.

[21] Appl. No.: 25,434

[22] Filed: Mar. 30, 1979

[30] Foreign Application Priority Data

Apr. 24, 1978 [DE] Fed. Rep. of Germany ....... 2817912
May 19, 1978 [DE] Fed. Rep. of Germany ....... 2821870

[51] Int. Cl.$^3$ ............................................ G03B 41/16
[52] U.S. Cl. ................................. 250/445 T; 250/360
[58] Field of Search ........................... 250/445 T, 360

[56] References Cited

U.S. PATENT DOCUMENTS 4,031,395  6/1977  Lemay ............................. 250/445 T
4,153,842  5/1979  Rohmfeld ......................... 250/445 T Primary Examiner—Craig E. Church
Attorney, Agent, or Firm—Thomas A. Briody; Robert T. Mayer; Jack E. Haken

[57] ABSTRACT

A device for examining an object with penetrating radiation, comprises a closed array of switchable radiation sources, which are arranged inside a flat disc-shaped space and enclose the object, and a closed array of transparent radiation detectors which is arranged within the array of radiation sources. During an examination, the radiation sources emit a beam of radiation which penetrates the neighboring detectors and irradiate the object from different directions. Transmitted radiation is measured by detectors which are situated behind the object.

14 Claims, 4 Drawing Figures

DEVICE FOR COMPUTED TOMOGRAPHY

The invention relates to a device for examining an object by means of penetrating radiation, comprising a closed array of radiation sources which are consecutively flashed and which serve to irradiate the object from different directions which of a beam of penetrating radiation, and a closed array of radiation detectors which measure radiation transmitted through the object.

A device of this kind is particularly suitable for use in a device for computed tomography; a part of the body of a patient is irradiated from different directions with a beam of X-rays and the density distribution of the body part is calculated from the measured radiation and is displayed, for example, on a television monitor. Because the X-ray beam is generated by a closed array of radiation sources which are consecutively flashed during examination to irradiate the patient from different directions, and because the transmitted radiation is measured by means of a closed array of radiation detectors, no mechanical movement of sources and detectors is required for performing an examination. As a result, an examination can be performed very quickly, so that moving parts of the body, for example the heart, can be imaged.

U.S. Pat. No. 4,031,395 describes a device of the kind set forth in which the array of radiation sources is arranged on a circle in a first plane and, the array of radiation detectors is arranged on a circle in a second plane which is parallel to the first plane.

When the known device is used for computed tomography, the calculation of the density distribution of the examined part of the body of the patient is very complex, because a non-flat area is irradiated by a curved beam of radiation; the central ray of the beam of radiation describes a circular cone.

The invention has for its object to provide a device of the described kind in which a flat area of an object is irradiated from different directions by a flat beam of radiation and the central ray of the beam of radiation moves in one plane. A device in accordance with the invention is characterized in that the radiation sources and the radiation detectors are arranged substantially in one plane, the radiation detectors being transparent to the penetrating radiation and being arranged within the array of radiation sources, viewed from the object. When a device of this kind is used in a device for computer tomography, the calculation of the density distribution of the examined part of the object can be comparatively simple performed.

A device of the described kind in accordance with the invention is preferably characterized in that the radiation detectors are arranged and shaped so that the beam of penetrating radiation generated by the radiation sources is substantially uniformly spatially attenuated by the radiation detectors (viewed from the object to be examined). Thus, the radiation emitted by the sources cannot reach the object to be examined without having been attenuated, which would mean a locally higher radiation intensity on the object. This locally higher radiation intensity would mean an overdose of radiation for the object, because the intensity of the radiation emitted by the sources should at least be so high that the intensity of the radiation attenuated by the detectors and incident on the object to be examined is still sufficient to perform radiation measurements with adequate measuring accuracy.

The radiation detectors in a device in accordance with the invention preferably absorb approximately 50% of the incident radiation. The radiation power of the radiation sources required for performing radiation measurements with a desired accuracy is a function of the fraction of the radiation absorbed by the radiation detectors. This function has a minimum value at which the fraction of absorbed radiation is 0.5.

The invention will be described in detail hereinafter, by way of example, with reference to the accompanying diagrammatic drawing.

Figure 1:
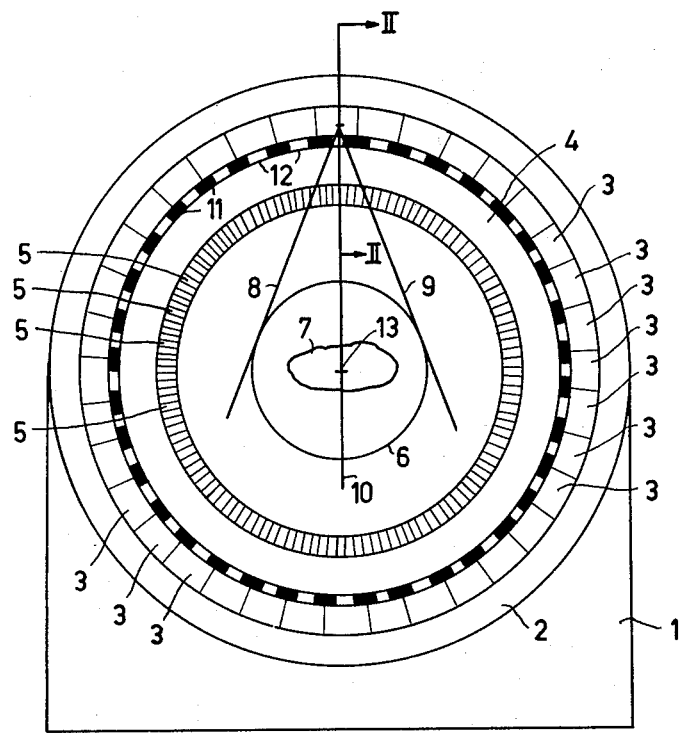
FIG. 1 is a cross-sectional view of a device in accordance with the invention.

FIG. 1 shows a device in accordance with the invention, comprising a base 1 with a supporting ring 2 on which a closed array of consecutively flashable radiation sources 3 is mounted. The drawing shows thirty-six radiation sources, but this number may in practice be much larger. The supporting ring 2 is connected to an annular plate 4 on which a closed array of radiation-transparent radiation detectors 5 is secured. The closed array of radiation sources 3 and the closed array of radiation detectors 5 enclose an examination area 6 in which an object 7 to be examined can be arranged. The radiation sources 3 and the radiation detectors 5 define a flat, disk-like space (they have comparatively small dimensions in the direction perpendicular to the plane of the drawing), so that only a thin slice of the object 7 is examined. During an examination, the radiation sources 3 consecutively emit a fan-shaped beam of radiation which penetrates the adjacent radiation detectors 5, as diagrammatically shown in the drawing for one source by way of extreme rays 8 and 9 and a central ray 10. During an examination, the object 7 is thus irradiated from different direction and the radiation transmitted by the object is measured by the radiation detectors 5. An annular aperture 11 is disposed between the ring of radiation detectors 5 and the ring of radiation sources 3. The aperture 11 is made, for example, of lead and comprises an opening 12 at each radiation source 3. The openings are proportioned so that the stopped beam just encloses the examination zone 6 and irradiates a flat slice of the object 7. No mechanical movement of sources or detectors is required for performing an examination; thus an examination can be very quickly performed so that moving objects, such as the beating heart of a patient, can be examined. During an examination a flat zone is irradiated by a flat beam, the central ray 10 of the beam rotating around the point 13, in the plane of the drawing. The measuring data obtained can be processed comparatively simply, for example, in a computer.

Figure 2:
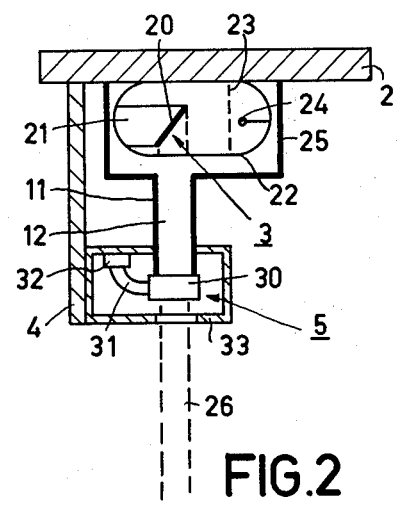
FIG. 2 is a sectional view, taken along the line II—II in FIG. 1.

FIG. 2 is a sectional view of the device shown in FIG. 1, taken along the line II—II The radiation source 3 is formed by a target 20 of a fixed anode 2 of an X-ray tube 22. The tube further comprises a control grid 23 and a cathode 24 which can be connected to earth potential. The X-ray tube 22, is connected to the supporting ring 2 and is accommodated in a housing 25 which is made of lead and which is also connected to the supporting ring 4. At the area of the target 20 of the anode 21 of the X-ray tube 22, the housing 25 is connected to the aperture 11. The aperture opening 12 serves to collimate the radiation to form a flat beam 26 having a thickness of, for example, 1 cm. The anodes 21 of all X-ray tubes 22 as well as the cathodes 24 of all X-ray tubes 22 may be connected to each other and to high voltage or earth, respectively. The grids 23 of all X-ray tubes are controlled via separate lines. X-ray tubes of the kind described in U.S. Pat. No. 4,031,395 may also be used.

Figure 3:
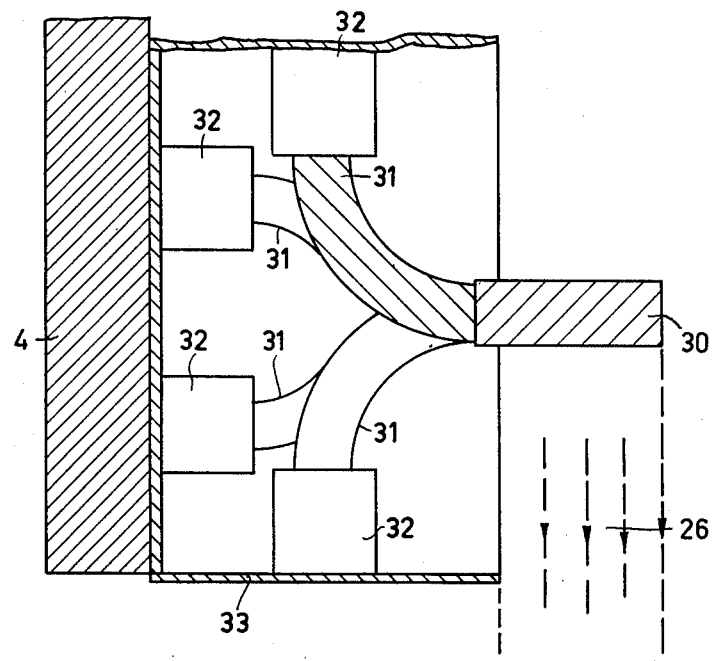
FIG. 3 shows a part of the sectional view of FIG. 2 at an increased scale.

The radiation detector 5 (shown in FIG. 1 and at an increased scale in FIGS. 2 and 3) is formed by a scintillator 30. The scintillation light produced by the absorption of radiation is applied, by means of a light conductor 31, to a light detector 32. The scintillator 30, for example a crystal of bismuth germanate, is protected against incident light by a chamber 33. The chamber 33 is connected to the annular plate which in its turn is connected to the supporting ring 2. Viewed from the object 7, the radiation detectors 5—the scintillators 30—form a closed array of adjoining radiation detectors, with the result that the radiation generated by the radiation source 3 is spatially substantially uniformly attenuated. A very thin light screen may be arranged between adjoining scintillators in order to suppress cross-talk between the scintillators. As a result of the uniform attenuation, locally high radiation intensities on the object 7 and hence a radiation overdose on the object 7 are avoided. The radiation detector 5 in the scintillator 30 preferably absorbs approximately 50% of the incident radiation, because the power of the radiation source 3 required for an examination is then minimum. FIG. 2 shows only one light conductor 31 and one light detector 32, while FIG. 3 shows a plurality of light conductors 31 and light detectors 32 accommodated in one common chamber 33. The scintillation detectors 30 which are arranged one behind the other in the direction transversely of the plane of the drawing are connected to associated light detectors 32 by means of curved light conductors 31.

Figure 4:
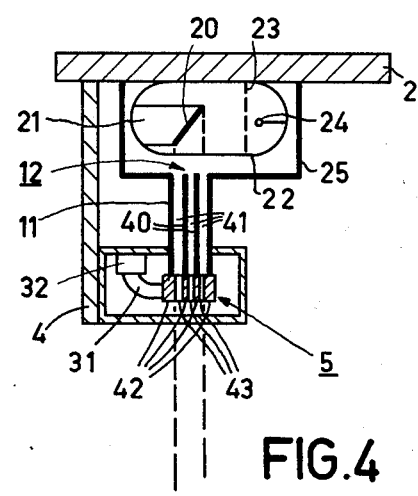
FIG. 4 is a sectional view of a part of a preferred embodiment of a device in accordance with the invention.

FIG. 4 shows a sectional view, corresponding to that of FIG. 2, of a preferred embodiment of a device in accordance with the invention; corresponding parts thereof being denoted by corresponding reference numerals from the FIGS. 1, 2 and 3. The aperture opening 12 of the aperture 11 comprises a number of radiation absorbing plates 40, two of which are shown in the drawing; however, in practice a larger number of such plates may be present. The plates subdivide the opening 12 into a number of slots 41 which collimate the radiation into the flat beam 26. Each radiation detector 5 comprises a number of scintillators 42 which are interconnected by radiation transmitting light conductors 43. Radiation emitted by the source 3 can reach the object to be examined in an unobstructed manner via the slots 41 and the light conductors 43. The radiation transmitted by the object is then measured by scintillators 42 of detectors which are situated behind the object 7, viewed from the radiation source (see FIG. 1). Besides the fact that in this preferred embodiment of the device the radiation beam 26 is very well collimated by the slots 41 in the aperture opening 12, the scintillators 42 of the detectors situated near an emitting source 3 are suitably shielded against radiation from this source by the absorbing plates 40 in the aperture opening 12. Thus the scintillators 42 are not exposed to radiation which—because the distance from the source is comparatively small—has a very high intensity. Afterglow effects might occur in the scintillators are thus prevented. These effects would adversely influence later measurements during an examination, unless so much time were to expire between the measurements that said afterglow effects would have disappeared; this, however, would prolong the examination time.

In a preferred embodiment of the detector 5 shown in FIG. 4, the thickness of the scintillators 42 substantially equals the thickness of the plates 40 in the aperture opening 12, the thickness of the light conductors 43 being substantially equal to the width of the slots 41 in the aperture opening 12. Moreover, the scintillators 42 substantially completely absorb the incident radiation. The overall thickness of the scintillators 42 amounts to approximately 50% of the width of the beam 26, and the overall thickness of the plate 40 hence equals approximately 50% of the width of the aperture opening 12, so that approximately 50% of the radiation generated reaches the object and approximately 50% of the radiation transmitted by the object is measured. Consequently, the radiation power of the radiation sources which is required for performing radiation measurements with a desired accuracy is minimum.

Detection output signals of radiation detectors 5 which are situated near an emitting source 3 are very suitable for use as a measure for the intensity of the radiation incident on the object 7. In the detector shown in FIG. 4, the output signal is produced in that in the light conductors 43 scattered radiation is generated by Compton effects, said scattered radiation causing scintillation light in the scintillators 42 which is measured in the light detectors 32.

What is claimed is:

1. A device for examining an object comprising:
   a plurality of individually controlled radiation source means, disposed in a planar array around the object, which function to irradiate the object, from different directions, with a beam of penetrating radiation, and
   a closed array of radiation detectors, disposed around the object within the array of source means and lying substantially in the plane thereof, the detectors functioning to measure radiation from the source means which is transmitted through the object and being at least partially transmissive of radiation from the source means to the object.

2. A device as claimed in claim 1 wherein the radiation detectors are disposed and shaped so that radiation generated by the source means is, when viewed from the object, substantially uniformly spatially attenuated by the radiation detectors.

3. A device as claimed in claim 2 wherein the radiation detectors absorb approximately fifty percent of radiation incident thereon.

4. A device as claimed in any of claim 1, 2 or 3 wherein each of the radiation detectors comprises a scintillator and a light detector, the light detector functioning to measure scintillation light produced in the scintillator, the radiation source means and scintillators being disposed within a disc-shaped space and light detectors being disposed outside of the disc-shaped space.

5. A device as claimed in claim 1, 2 or 3 wherein each of the radiation detectors comprises:
   a plurality of scintillators;
   light detector means which function to measure light produced by the scintillators; and a plurality of light conductors which transmit the light from the scintillators to the light detector means and which are transmissive of the penetrating radiation;

the radiation source means and scintillators being disposed within a disc-shaped space and the light detector means being disposed outside of the disc-shaped space.

6. A device as claimed in claim 4 wherein each of the radiation detectors comprises:

a plurality of scintillators;

light detector means which function to measure light produced by the scintillators; and a plurality of light conductors which transmit the light from the scintillators to the light detector means and which are transmissive of the penetrating radiation;

the radiation source means and scintillators being disposed within a disc-shaped space and the light detector means being disposed outside of the disc-shaped space.

7. A device as claimed in claim 5 wherein each of the radiation detectors comprises:

a plurality of radiation absorbing scintillators which are spaced, one from the other, to define a plurality of radiation transmitting apertures;

and further comprising a radiation absorbing shield is disposed between each of the radiation absorbing scintillators and adjacent source means.

8. A device as claimed in claim 6 wherein each of the radiation detectors comprises:

a plurality of radiation absorbing scintillators which are spaced, one from the other, to define a plurality of radiation transmitting apertures;

and further comprising a radiation absorbing shield is disposed between each of the radiation absorbing scintillators and an adjacent source means.

9. A device as claimed in claims 1, 2 or 3 wherein at least one radiation detector which is disposed between a radiation source means and the object further functions to measure the intensity of radiation which is incident on the object from that source.

10. A device as claimed in claim 4 wherein at least one radiation detector which is disposed between a radiation source means and the object further functions to measure the intensity of radiation which is incident on the object from that source.

11. A device as claimed in claim 5 wherein at least one radiation detector which is disposed between a radiation source means and the object further functions to measure the intensity of radiation which is incident on the object from that source.

12. A device as claimed in claim 6 wherein at least one radiation detector which is disposed between a radiation source means and the object further functions to measure the intensity of radiation which is incident on the object from that source.

13. A device as claimed in claim 7 wherein at least one radiation detector which is disposed between a radiation source means and the object further functions to measure the intensity of radiation which is incident on the object from that source.

14. A device as claimed in claim 8 wherein at lest one radiation detector which is disposed between a radiation source means and the object further functions to measure the intensity of radiation which is incident on the object from that source.

* * * * *